(12) United States Patent
Schnyder et al.

(10) Patent No.: US 6,443,007 B1
(45) Date of Patent: Sep. 3, 2002

(54) FLUID FOR MEASURING VOLUME, DENSITY AND RELATED PROPERTIES OF SOLID BODIES

(75) Inventors: Max Schnyder, Stäfa; Bruno Nufer, Illnau, both of (CH)

(73) Assignee: Mettler-Toledo GmbH, Greifensee (CH)

(*) Notice: Subject to any disclaimer, the term of this patent is extended or adjusted under 35 U.S.C. 154(b) by 0 days.

(21) Appl. No.: 09/560,023

(22) Filed: Apr. 27, 2000

(30) Foreign Application Priority Data

Apr. 27, 1999 (DE) .......................... 199 19 011

(51) Int. Cl.$^7$ .......................... G01N 9/00; G01F 17/00
(52) U.S. Cl. .......................... 73/437; 177/207
(58) Field of Search .......................... 73/32 R, 433, 73/434, 437; 177/1, 25.19, 165, 207

(56) References Cited

U.S. PATENT DOCUMENTS

| | | | | | |
|---|---|---|---|---|---|
| 3,073,272 A | * | 1/1963 | Swallert | .................. | 73/437 |
| 3,244,010 A | * | 4/1966 | Martin | .................. | 73/437 |
| 3,747,416 A | * | 7/1973 | Wommack | .................. | 73/437 |
| 3,835,711 A | * | 9/1974 | Kelley | .................. | 73/444 |
| 3,871,489 A | * | 3/1975 | Patigalia | .................. | 73/433 |
| 4,196,618 A | * | 4/1980 | Patterson | .................. | 73/437 |
| 4,372,405 A | * | 2/1983 | Stuart | .................. | 73/437 |
| 4,770,041 A | * | 9/1988 | Kearce | .................. | 73/437 |
| 4,887,231 A | * | 12/1989 | Ratliff et al. | .................. | 73/149 |

* cited by examiner

*Primary Examiner*—Helen Kwok
(74) *Attorney, Agent, or Firm*—Friedrich Kueffner

(57) ABSTRACT

In a method for measuring density and related properties by weighing a solid body while it is suspended in a fluid, there are significant advantages if the fluid has a) a density that is smaller than the density of water;
b) a surface tension that is significantly smaller than the surface tension of water;
c) a rate of evaporation that is slower than the evaporation rate of water, due to a vapor pressure that is smaller than the vapor pressure of water-by at least a factor of 2; and
d) a water absorption of less than 1%. Preferably, the fluid contains at least one cyclosilane.

10 Claims, No Drawings

FLUID FOR MEASURING VOLUME, DENSITY AND RELATED PROPERTIES OF SOLID BODIES

BACKGROUND OF THE INVENTION

The present invention belongs to the field of density measurement and relates to a fluid for measuring the density or related properties (e.g., volume, specific gravity) of solid bodies, as well as a method and apparatus for performing the measurement.

The density of solid bodies is commonly determined by weighing the body in air (dry weight) and subsequently weighing the same body in a fluid (wet weight), normally in water. The density, specific gravity, or volume of the solid body is then calculated in an essentially known manner from the dry and wet weight values. Various versions of essentially the same method are known where, e.g., an entire balance is immersed in a fluid, or the container that holds the fluid is weighed while the solid body under test is suspended from a fixed point into the fluid.

The process (in any of its various forms) is known to work well for solid bodies of higher density than water. However, a complication occurs with bodies of lesser density, because such bodies will float on the surface of the water. This has led to a method of measuring solid bodies of lesser density in an alcoholic medium instead of water. A closer examination of the measuring results achieved with alcohol has shown, however, that accuracy and reproducibility are unsatisfactory for at least a number of practical applications. Alcohol has a high volatility and, therefore, alcoholic mixtures have a variable density.

Distilled water can be handled without problems as a medium for density determinations. However, it has a relatively strong tendency to absorb gases, particularly $CO_2$, combined with a relatively week tendency of wetting the surfaces of immersed objects. It is possible for gas bubbles to attach themselves to rough surfaces and falsify the results. Methods are known for degassing fluids by means of ultrasound but this involves a need for additional equipment, and it adds a certain amount of energy to the fluid with the result of an increase in temperature. Other fluids are known to be usable for density determinations, but they can overcome no more than a part of the aforementioned disadvantages. For example, the fluid known as FC 40 has good wetting properties, but with a density of 1.8 $g/cm^3$, it is suitable only for measurements of solid bodies of high density or for methods of measuring the density of floating bodies. In addition, it is fairly volatile, which causes its density to be variable.

OBJECT OF THE INVENTION

It is therefore the object of the present invention, to provide a fluid, a method, as well as an apparatus, by which the density and related properties of solid bodies can be measured with a higher degree accuracy and reproducibility.

SUMMARY OF THE INVENTION

Based on extensive serial experiments performed by the inventor(s), it was found that the aforementioned object of the invention can be met with a fluid with the properties that
a) The density of the fluid is smaller than the density of water;
b) The surface tension is significantly smaller than the surface tension of water;
c) The rate of evaporation is slower than the evaporation rate of water, the vapor pressure of the fluid being smaller than the vapor pressure of water by at least a factor of 2;
d) The water absorption, i.e., the hygroscopicity of the fluid is less than 1%.

Having knowledge of this advantageous combination of properties, a person skilled in the art will require little effort to find a fluid that meets the stated characteristics.

In principle, a low level of volatility of the fluid is desirable. Alcohol, in particular, does not meet this requirement. According to the invention, it is advantageous to use a fluid with a vapor pressure that is smaller than the vapor pressure of water by at least a factor of 4.

Of course, the scope of the invention also covers the use of mixtures of fluids. To obtain good results in this case, it is important to use an approximately azeotropic mixture. By definition, this is a mixture in which all components have essentially the same boiling point, so that there is no separation or change in the composition of the mixture due to different amounts of evaporation over an extended period of time, which would cause a change in the properties of the mixture. Nearly azeotropic mixtures in a variety of compositions have been proposed, e.g., as replacements for fluids containing fluorocarbons, so that a person skilled in the art and equipped with a knowledge of the present invention will have a choice of fluids available.

One problem in using fluids other than water lies in the naturally occurring moisture in the atmosphere, which can affect the properties of the fluid. For this reason, the use of fluids with no more than 0.5% water absorption and, in particular, less than 0.1% is preferred according to the invention.

While the known use of water in density determinations presents no problem in regard to environmental compatibility or toxicity, there can be certain problems in this regard when using another fluid. It is therefore advantageous to use a fluid that contains no fluorocarbon chlorides and is nontoxic.

Another obvious problem that could occur with a fluid other than water is flammability. It is a particular advantage of the invention that fluids with the aforementioned characteristics are available that have flash points above 50° C. and self-ignition points above 350° C., i.e., fluids that are non-critical with regard to flammability.

In the experiments and tests performed by the inventor(s), it was found that excellent results, at least by an order of magnitude more accurate, are obtainable by using a fluid containing at least one silicon hydride. Silicon hydrides, also called silanes according to IUPAC rule D-6.14h, include branched as well as unbranched silicon hydrides. Substitutions such as, e.g., silyls, are also entirely within the scope of the invention. Particularly preferred are cyclosilanes as they meet most of the required characteristics mentioned above, for example alcoholic cyclosilanes in which at least one alcohol group such as an ethyl-, methyl-, buthyl-, propyl-, iso-propyl alcohol or the like is attached to the silicon atom. Of course, these or similar alcohols can be substituted by esters (generally of the low-valence kind), in fewer cases also by ether. Particularly preferred are fluids in which the alcohol group attached to the silicon atom is a methyl group.

Cyclosilanes with at least four silicon atoms, i.e., relatively large ring formations, are preferred. In these formations, it is preferable to have at least two alcohol groups attached to each silicon atom, particularly in a branched configuration.

DETAILED DESCRIPTION OF THE PREFERRED EMBODIMENT

In practical applications, octamethyl-cyclotetrasiloxane and higher-order ring formations such as dekamethyl-cyclopentasiloxane have been proven to produce excellent results. The surfactant properties (surface tension of 18 to 19 N/m at 25° C.) have turned out to be a particularly favorable trait of these compounds in that they prevent the formation—or promote the rapid disappearance—of gas bubbles that cling to the surface of the solid body being tested and are detrimental to the accuracy of the measurement. It should be noted that cyclo-silanes of this kind are commercially available for different applications, e.g., as coolants, detergents, and solvents, and that they have the following distinctive combination of properties: Their density is less than 1 g/cm³; they have a low toxicity, allowing them to be sold without restriction; their self-ignition temperature is 390–400° C. and higher; their flash point is between 50 and 80° C.; their hygroscopicity (water absorption) does not exceed 0.1%; their vapor pressure is lower than for water by a factor of 4; they generally maintain their physical properties over time at different temperatures; and they have good wetting properties (even to the extent of eliminating the need for the degassing step that is common with water). Many of the fluids that contain cyclosilanes of these kinds are nearly azeotropic mixtures.

The following examples are intended to illustrate the advantages of the fluids described above. Density determinations were performed on articles made of polymer materials with an irregular surface and a density of close to 1 g/cm³, i.e., articles that are difficult to measure by the conventional method.

EXAMPLE 1

The density of a circuit board of an electronic watch had to be determined. Its dry weight was 0.2441 g. In a first test series, five weighings were made of the same sample in water as a basis for comparison. With the formula $$d = \frac{dry\ weight \times (d_0 - d_L)}{dry\ weight - wet\ weight} + d_L$$

in which $d_o$ represents the density of the fluid and $d_L$ represents the average air density, results for density were obtained in the respective amounts of 1.610, 1.628, 1.598, 1.640, and 1.640 g/cm³. Thus, The results were scattered over a range of 0.042 g/cm³.

In a second test series, a nearly azeotropic mixture of about 75% (by weight) octamethyl-cyclotetrasiloxane and 25% (by weight) dekamethyl-cyclopentasiloxane was used to measure the density of the same circuit board. The density of this mixture at 25° C. was 0.952 g/cm³. The dry weight of the watch housing shell was the same as given above. The respective results from five measurements, using again the foregoing equation, were 1.655, 1.654, 1.654, 1.654, and 1.655 g/cm³, corresponding to a scatter range of only 0.002 g/cm³. Thus, using a fluid according to the invention increased the accuracy and reproducibility of the measurement by more than an order of magnitude.

EXAMPLE 2

The same comparison was performed with a different object, a small rubber bumper. Its dry weight was 0.5028 g. Five measurements in water produced density values of 1.410, 1.412, 1.406, 1.410, and 1.405 g/cm³. This corresponds to a scatter range of only 0.007 g/cm³, which could already be considered a good result.

However, a still superior result was obtained by using the mixture described in example 1, with density values of 1.414, 1.414, 1.414, 1.414, and 1.415 g/cm³. Thus, the scatter range was only 0.001 g/cm³.

EXAMPLE 3

Using the fluid of example 1, a further comparative test was made with a plastic support bracket. The dry weight was 0.7256 g. The respective density values from five measurements in water were 1.582, 1.607, 1.619, 1.612, and 1.619 g/cm³, corresponding to a scatter range of 0.037 g/cm³.

Using the nearly azeotropic mixture of example 1, the resulting density values were 1.623, 1.623, 1.623, 1.624, and 1.622 g/cm³, corresponding to a scatter range of 0.002 g/cm³.

EXAMPLE 4

In this experiment, an axle with two plastic O-rings was tested. The dry weight was 0.9007 g, and the respective density values from five measurements in water were 1.515, 1.515, 1.515, 1.498, and 1.498 g/cm³, corresponding to a scatter range of 0.017 g/cm³.

Using the same mixture as in the previous examples, the resulting density values were 1.520, 1.519, 1.519, 1.519, 1.519 g/cm³, corresponding to a scatter range of only 0.001 g/cm³.

EXAMPLE 5

In this example, a Teflon™ enclosure cap of 1.8940 g dry weight was tested. The respective density values from five measurements in water were 2.143, 2.142, 2.145, 2.142, and 2.146 g/cm³, i.e., the scatter range was only 0.004 g/cm³.

In contrast, when the wet weight was measured in the mixture of the previous examples, the resulting density values were 2.147, 2.148, 2.146, 2.146, and 2.148 g/cm³, corresponding to an even lower scatter range of 0.002 g/cm³.

Additional experiments were performed using a different composition of the mixture. One formulation contained (by weight) about 95% octamethyl-cyclotetrasiloxane and 5% dekamethyl-cyclopentasiloxane (Density at 25° C.: 0.951 g/cm³), while another formulation used the reverse ratio of the two compounds (Density at 25° C.: 0.956 g/cm³). In both cases, the scatter of the results was similar to the foregoing examples. Throughout, the scatter values for the mixture of 5% octamethyl-cyclotetrasiloxane and 95% dekamethyl-cyclopentasiloxane were somewhat inferior to the foregoing examples, perhaps because the density of this mixture is closer to the density of water, but the scatter was still better than with the conventional use of water.

In particular, the latter mixture exhibited a very favorable trait under temperature variations in that the relationship between density and temperature was practically linear between 14 and 30° C., decreasing from 0.965 to slightly under 0.95 g/cm³. With the rest of the mixtures tested as reported above, this phenomenon was significantly less pronounced.

The conclusion from the various comparative tests was that other, similar fluids could be used to good advantage, as long as the criteria stated above in the summary of the invention are met. The fluid can be used in a method for measuring volume, density and related properties of solid bodies and also in a measuring apparatus for performing these measurements. As such, the fluid according to the invention also represents an inventive enhancement of a conventional instrument for measuring the density of solid bodies where the solid body is weighed while immersed in a fluid, in which case the practice of the invention consists of replacing the conventionally used water with the fluid possessing the aforementioned distinguishing properties.

What is claimed is:

1. A method for measuring density and related properties of a solid body, comprising a step wherein a weighing is performed in which the solid body is suspended into a fluid with
   a) a density that is smaller than the density of water;
   b) a surface tension that is significantly smaller than the surface tension of water;
   c) a rate of evaporation that is slower than the evaporation rate of water, due to a vapor pressure that is smaller than the vapor pressure of water by at least a factor of 2; and
   d) a water absorption of less than 1%.

2. The method of claim 1, wherein the vapor pressure is smaller than the vapor pressure of water by at least a factor of 4.

3. The method of claim 1, wherein the fluid is a nearly azeotropic mixture.

4. The method of claim 1, wherein the water absorption does not exceed 0.5%.

5. The method of claim 1, wherein the water absorption does not exceed 0.1%.

6. The method of claim 1, wherein the fluid is free of fluorocarbon chlorides and non-toxic.

7. The method of claim 1, wherein the fluid comprises at least one non-toxic silicon hydride.

8. The method of claim 7, wherein the at least one silicon hydride is a cyclo-silane.

9. The method of claim 8 where, on the cyclo-silane, at least one hydrocarbon group is replaced by another type of hydrocarbon group.

10. A measuring apparatus for measuring density and related properties of a solid body, the apparatus comprising a weighing scale and a container holding a fluid into which the solid body is immersed while the weighing is performed, the fluid having
    a) a density that is smaller than the density of water;
    b) a surface tension that is significantly smaller than the surface tension of water;
    c) a rate of evaporation that is slower than the evaporation rate of water, due to a vapor pressure that is smaller than the vapor pressure of water by at least a factor of 2; and
    d) a water absorption of less than 1%.

* * * * *